United States Patent [19]

Partridge et al.

[11] Patent Number: 5,576,430
[45] Date of Patent: Nov. 19, 1996

[54] 1,8-DIAZABICYCLO[5.4.0]UNDEC–1(7)–ENIUM CYANIDE AND METHOD OF MAKING THEREOF

[75] Inventors: John J. Partridge, Chapel Hill; Brian L. Bray, Graham, both of N.C.

[73] Assignee: Glaxo Wellcome Inc., Research Triangle Park, N.C.

[21] Appl. No.: 271,594

[22] Filed: Jul. 7, 1994

Related U.S. Application Data

[62] Division of Ser. No. 44,339, Apr. 7, 1993, Pat. No. 5,329,008.

[51] Int. Cl.$^6$ ............... C07D 487/04; C07D 473/18; C07B 35/08
[52] U.S. Cl. ............. 540/523; 544/276; 544/265; 544/277
[58] Field of Search ............................... 540/523

[56] References Cited

PUBLICATIONS

Jammot, J. et al. "Hydration of Cyanohydrins in Weekly Alkaline Solutions of Boric Acid Salts", *Tetrhed. Lett.* 30, 563–564 (1989).

Fieser, M. *Fieser and Fieser's Reagents for Organic Synthesis*, vol. 12 (Wiley, New York), p. 156 (1986).

Morrison, R. T. et al. *Organic Chemistry* (Allyn and Bacon, Boston), p.217 (1987).

Palmer, D. C. et al. "Meta Bridging Reactions. II. The first Reported Nucleophilic Additions of Diazabicyclononene". *Tetrahed Lett.* 18, 1431–1434 (1976).

Fieser, M. *Fieser's Reagents for Organic Synthesis*, vol. 9 (Wiley, New York), p. 133 (1981).

*Primary Examiner*—Mukund J. Shah
*Assistant Examiner*—King Lit Wong
*Attorney, Agent, or Firm*—James P. Reik; Gardiner F. H. Smith

[57] ABSTRACT

The compound 1,8-diazabicyclo[5.4.0]undec-1(7)-enium cyanide is the reaction product of acetone cyanohydrin and 1,8-diazabicyclo [5.4.0]undec-7-ene.

2 Claims, No Drawings

1,8-DIAZABICYCLO[5.4.0]UNDEC–1(7)–ENIUM CYANIDE AND METHOD OF MAKING THEREOF

This is a division of U.S. Ser. No. 08/044,339, filed 7 Apr. 1993, which issued as U.S. Pat. No. 5,329,008 on Jul. 12, 1994.

BACKGROUND OF THE INVENTION

Carbocyclic analogues of nucleosides are described in European Patent Application Publication No. 345,076 published Dec. 6, 1989 as being useful as pharmaceuticals in the treatment of viruses, especially Herpetoviridae. A particular compound described is (1'S, 3'S, 4'S)-2-amino-1,9-dihydro-9-[3,4-dihydroxy-3-(hydroxymethyl)-1-cyclopentyl]-6H-purin-6-one of the following formula (I):

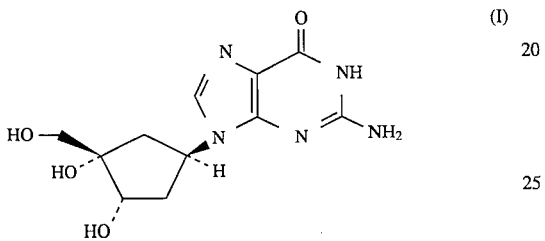

European Patent Application Publication No. 349,242 published Jan. 3, 1990 assigned to the Wellcome Foundation teaches 6-substituted purine carbocyclic nucleosides and Example 45 provides a synthesis of (±)-9-[3-(hydroxymethyl)-3-cyclopenten-1-yl)guanine (racemic compound of formula (X)). A process for synthesizing 2-amino-1,9-dihydro-9-[2,3-dihydroxy-4-(hydroxymethyl)-1-cyclopentanyl]-6H-purin-6-one is taught in U.S. Pat. No. 5,110,926 using hydrolysis as a final step. U.S. patent application Ser. No. 07/772,738 teaches the synthesis of (1'S, 3'S, 4'S)-2-amino-1,9-dihydro-9-[3,4-dihydroxy-3-(hydroxymethyl)-1-cyclopentanyl]-6H-purin-6-one using a Swern oxidation. U.S. patent application Ser. No. 07/505,809 teaches the synthesis of (−)-carbovir, 2-amino-1,9-dihydro-9-[3-(hydroxymethyl)-1-cyclopentenyl]-6H-purin-6-one.

SUMMARY OF THE INVENTION

The present invention comprises the compound 1,8-diazabicyclo[5.4.0]undec-1(7)-enium cyanide as the reaction product of acetone cyanohydrin and 1,8-diazabicyclo[5.4.0]undec-7-ene.

DETAILED DESCRIPTION OF THE INVENTION

The present invention includes the method of synthesizing a triol of the following formula (I):

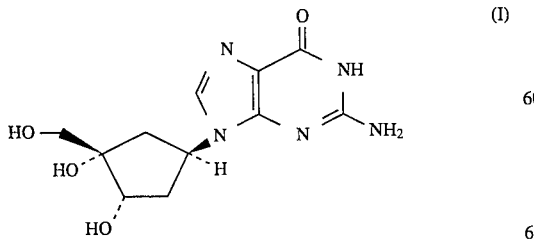

or an acid- or base-addition salt thereof, which comprises the steps of:

i) reacting a cyclopentene of the following formula (II):

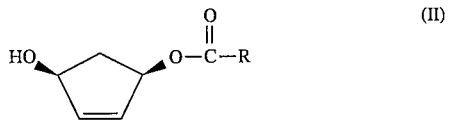

wherein $R=C_{1-6}$alkyl or $OC_{1-6}$alkyl, with a purine of the following formula (III):

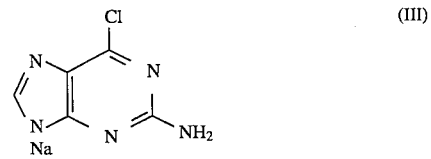

to yield an alcohol of the following formula (V):

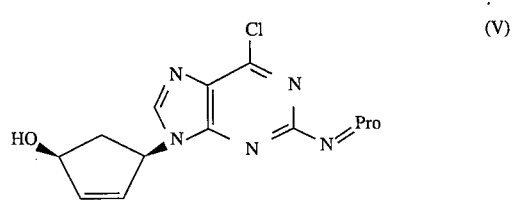

wherein Pro is an amino protecting group, ii) cyanating the alcohol of formula (V) to yield the cyanide of the following formula (VIII):

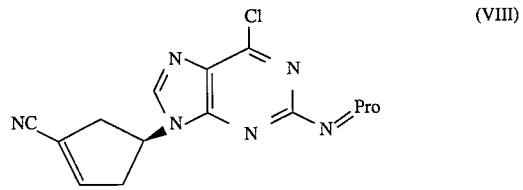

iii) deprotecting, hydrolyzing, and then reducing the cyanide of formula (VIII) to yield the monoalcohol of the following formula (X):

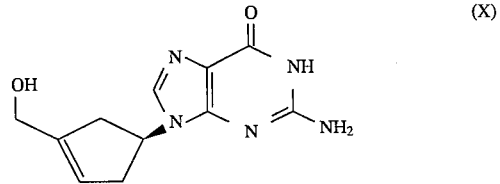

iv) cis-dihydroxylatingon the monoalcohol of formula (X) to produce the triol of formula (I).

Reaction Scheme 1 which follows sets forth the overall sequence of steps which may be used in carrying out the invention. The compound of formula (IV) in the following Reaction Scheme 1 is reacted with an amine protecting reagent whereby the amino function cannot react with reactants in the subsequent steps. Thus, Pro in formulae (V), (VI), (VII) and (VIII) represents a moiety bound by a double bond, or 2 moieties bound by 2 single bonds, to the pendent amino nitrogen, e.g. $=CN(CH_3)_2$ or —H and —CHO. Although various amine protecting groups can be used, use of an aminal, also known as an amidine or formamide, has the added benefit of rendering the molecule more soluble in organic solvents so as to allow the subsequent reactions to proceed more readily. Reaction with the amine protecting group reagent can be at about 0° to 35° C. in an organic solvent such as methanol, benzene, or dimethylformamide. Removal of the amine protecting group can be carried out by techniques including acid- or base-catalyzed hydrolyses or hydride reduction. In more detail the hydrolysis can be carried out with acids such as hydrochloric acid and sulfuric acid and the like or bases such as potassium hydroxide, sodium hydroxide, sodium methoxide, and the like or pyridine and triethylamine and the like in protic solvents such as water, methanol, ethanol, and the like. An amine protecting group =CN(CH$_3$)$_2$ can also be removed by hydride reduction with metal hydrides such as sodium borohydride and the like in protic solvents water, methanol, ethanol, and the like.

From formula (V), the compound of formula (VI) is produced by sulfonation, in particular via a substitution with a methanesulfonyl or p-toluenesulfonyl moiety, also known as mesyl or tosyl groups, to produce the mesylate or tosylate. Reagents for this reaction include pyridine, methylene chloride and methanesulfonic anhydride or p-toluenesulfonic anhydride, which may be reacted at a temperature of −15° to 15° C. The compound of formula VI is shown in brackets to indicate that it may not be isolatable. The compound of Reaction Scheme 1:

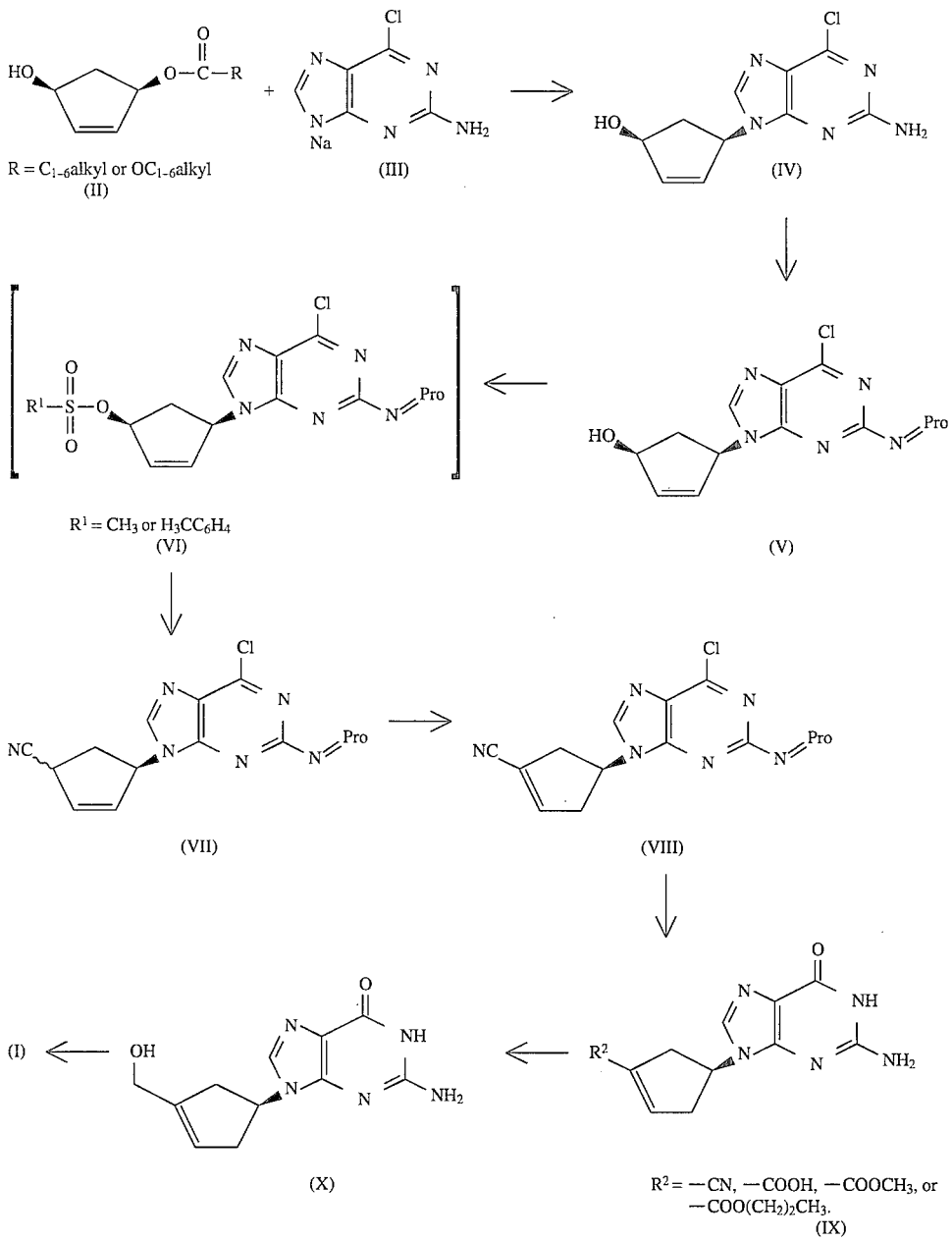

The cyclopentene of formula (II) is reacted with the purine of formula (III) to give the alcohol of formula (IV). The amine substituent of the compound of formula (IV) is then reacted with an amine protecting reagent such as dimethylformamide dimethylacetal to yield the alcohol of formula (V), e.g. where Pro is a formamidine group.

formula (VI) is then converted to the cis-trans mixture of the cyanide of formula (VII) by reaction with a cyanide ion from the phase transfer catalyst produced by the reaction of acetone cyanohydrin and 1,8-diazabicyclo[5.4.0]undec-7-ene. Isomerization of the cyclopentene double bond into conjugation with the nitrile may be carried out in a 1,8- diazabicyclo[5.4.0]undec-7-ene/hydrogen cyanide buffered organic phase to produce the compound of formula (VIII).

Deprotection of the amino substituent of the compound of formula (VIII) to a compound of formula (IX) where $R^2$ is —CN is conducted in the presence of hydrochloric acid, sulfuric acid, p-toluenesulfonic acid or a similar strong acid at about 60° to 90° C. The cyanide of formula (IX) where $R^2$ is —CN may be hydrolyzed to the carboxylic acid of formula (IX) where $R^2$ is —COOH. The carboxylic acid of formula (IX) where $R^2$ is —COOH may then be converted to the ester of formula (IX) where $R^2$ is COOCH$_3$, e.g. in the presence of methanol and sulfuric acid at a temperature of 60° to 90° C. Alternatively, the cyanide of formula (IX) where $R^2$ is —CN may be hydrolyzed to the compound of formula (IX) where $R^2$ is —COO(CH$_2$)$_2$CH$_3$. Hydrolyzing the cyanide of formula (IX) to the carboxylic acid of formula (IX) may be carried out in the presence of aqueous sodium hydroxide at a temperature of 60° to 90° C. Hydrolizing the cyanide to the acid may also be carried out with potassium hydroxide, triethylamine or a similar organic or inorganic base. Hydrolyzing the cyanide of formula (IX) to the compound of formula (IX) where $R^2$ is —COO(CH$_2$)$_2$CH$_3$ may be carried out in the presence of propanol and sulfuric acid at a temperature of 85° to 115° C. The compound of formula (IX) where $R^2$ is —COOCH$_3$ or —COO(CH$_2$)$_2$CH$_3$ is reduced in the presence of methylene chloride and diisobutylaluminum hydride at about −10° to 35° C. to give the compound of formula (X).

The compound of formula (X) may then be specifically 1,2-cis-dihydroxylated with a catalyst such as osmium tetroxide (OsO$_4$) and an oxygen source to afford a compound of the formula (I). Reviews of osmium tetroxide oxidations include those of Martin Schroeder in Chemical: Reviews, 1980, 80, pp187–213 and V. VanRheenen in Tetrahedron Letters, No.23, pp1973–1976. In general, the reaction of (X) to (I) may be conducted in an H$_2$O:acetone mixture having a ratio of 1:1 to 50:1, at about 0° to 100° C., e.g. 23° C., with about 0.008 to 1 equivalent of osmium tetroxide and an oxygen source such as hydrogen peroxide, N-methylmorpholine N-oxide, a metal chlorate, t-butyl hydroperoxide, sodium peroidate, oxygen gas or sodium hypochlorite.

Also part of the present invention are novel intermediates, e.g. formulae (IV), (V), (VI), (VII), (VIII), and (IX) and all enantiomers and diastereomers thereof.

Further parts of the present invention include triols of formula (I) in the form of the i) hydrochloride, ii) hydrochloride monohydrate, iii) hemihydrochloride monohydrate. The hydrochloride monohydrate is particularly important since it has a relatively lower melting point than other salts, is not hydroscopic and becomes increasingly pure through repeated recrystallizations and is thus suitable for use as an active ingredient in a formulated pharmaceutical.

The present invention also covers the individual enantiomers of the compounds represented by Reaction Scheme 1 above as mixtures with diastereoisomers thereof in which one or more stereocenters is inverted.

In the following Examples and throughout the specification, the following abbreviations may be used: mg (milligrams); g (grams); ml (milliliters); hr (hours); min (minutes); mp (melting point); mmole (millimoles); MeOH (methanol); and DMSO (dimethyl sulfoxide); CH$_2$CL$_2$ (methylene chloride); DMF (dimethylformamide). Unless otherwise noted, all temperatures are expressed in °C. (degrees centigrade).

EXAMPLE 1

2-Amino-6-chloropurine Sodium Salt
(Formula (III))

A 2 L round bottomed flask was charged with 100 g (0.59 mole) of 2-amino-6-chloropurine and 1 L of methanol. To the stirred slurry was added a 137 mL (0.59 mole) of a 4.3M solution of sodium methoxide in methanol. The slurry became homogeneous after stirring for 15 minutes at 23° C. The reaction mixture was stirred an additional 15 minutes, then vacuum filtered through paper. The filtrate was transfered to a 2 L round bottom flask and the solvent volume was reduced to 370 ml to induce crystallization. To complete crystallization, 500 mL of diethyl ether was added to the stirred slurry over 30 minutes. The solids were collected by vacuum filtration, washed with 100 mL of diethyl ether and dried under vacuum (0.5 mm, 23° C.) for 12 hrs to yield 93 g (82%) of 2-amino-6-chloropurine sodium salt.

mp>280° C.

EXAMPLE 2

(1'R-cis)-2-Amino-1,9-dihydro-9-[4-hydroxy-2-cyclopenten-1-yl]-6-chloropurine Dimethylaminal
(Formula (V))

a. (1'R-cis)-2-Amino-1,9-dihydro-9-[4-hydroxy-2-cyclopenten-1-yl]-6-chloropurine (formula (IV))

To a 500 mL round bottomed flask containing a solution of 1.62 g (1.80 mmole) of tris(dibenzylideneacetone)dipalladium (0) in 105 mL of tetrahydrofuran was added 1.8 mL (22.1 mmole) of chloroform. The deep violet solution was stirred at 23° C. for 2 minutes, then 3.71 g (14.2 mmole) of triphenylphosphine was added. The solution turned amber in color while stirring at 23° C. After 15 minutes, a solution of 17.0 g (88.5 mmole) of 2-amino-6-chloropurine sodium salt, prepared as in Example 1, in 105 mL of dimethylformamide was added followed by the neat addition of 15.1 g (106 mmole) of (+)-(1R-cis)-4-cyclopentene-1,3-diol monoacetate of formula (II). The reaction mixture was stirred at 23° C. for 75 minutes, then poured into a 4 L separatory funnel containing 400 mL of 2.4N aqueous hydrogen chloride. The aqueous solution was washed two times with 250 mL of methylene chloride, then with 250 mL of ethyl acetate. The organic extracts were discarded. The pH of the aqueous solution was adjusted to 7 with 70 mL of 30% aqueous ammonium hydroxide. The aqueous solution was extracted 5 times with 250 mL of ethyl acetate. The combined organic extracts were dried over 25 g of magnesium sulfate, filtered and concentrated to give 26.2 g of crude (1'R-cis)-2-Amino-1,9-dihydro-9-[4-hydroxy-2-cyclopenten-1-yl]-6-chloropurine of formula (IV) as an oil contaminated with dimethylformamide (2.5 eq by $^1$H NMR).

b. (1'R-cis)-2-amino-1.9-dihydro-9-[4-hydroxy-2-cyclopenten-1-yl]-6-chloropurine dimethytlaminal (Formula (V))

26.2 g of crude (1'R-cis)-2-Amino-1,9-dihydro-9-[4-hydroxy-2-cyclopenten-1-yl]-6-chloropurine, prepared as in Example 2a, as an oil contaminated with dimethylformamide (2.5 eq by $^1$H NMR) was dissolved in 450 mL of acetonitrile then transferred to a 1 L round bottomed flask equipped with a magnetic stir bar and reflux condenser. The reaction vessel was placed in an oil bath preheated to 65°–70° C. and 12.9 mL (97.5 mmole) of dimethylformamide dimethylacetal was added. The solution was stirred at 65° C. for 30 minutes. To induce crystallization, the solvent volume was reduced to 125 mL. To complete crystallization, the slurry was cooled to 0° C. while stirring and 100 mL of a 1:1 solution of diethyl ether/hexane was added over 30 minutes. The slurry was stirred at 0° C. for 2 hours, the crystals were collected by vacuum filtration and dried under vacuum (0.5 mm, 23° C.) for 15 hours to yield 12.6 g (46%) of the title compound.

mp 187°–189° C.

$[\alpha]_D$+202° (c 0.0966, $CH_2Cl_2$).

Analysis Found: C (51.02), H (4.98), N (27.23), Cl (11.74); $C_{13}H_{15}ClN_6O$ requires: C (50.90), H (4.93), N (27.40), Cl (11.56).

EXAMPLE 3

(1'S)-2-Amino-1,9-dihydro-9-[4-cyano-3-cyclopenten-1-yl]-6-chloropurine Dimethylaminal (Formula (VIII))

A 1 L round bottomed flask equiped with a magnetic stir bar and gas inlet vented through a nitrogen atmosphere was charged with 12.2 g (39.8 mmole) of (1'R-cis)-2-amino-1,9-dihydro-9-[4-hydroxy-2-cyclopenten-1-yl]-6-chloropurine dimethytlaminal, prepared as in Example 2, 11.0 g (139 mmole) of pyridine and 180 mL of methylene chloride. The solution was cooled to 0° C. under an atmosphere of nitrogen. A solution of 13.9 g (79.5 mmole) of methanesulfonic anhydride in 60 mL of methylene chloride was added to the stirred solution over 1 minute. The reaction mixture was stirred at 0° C. for 20 minutes to give a compound of formula (VI), then 27.1 g (318 mmole) of acetone cyanohydrin was added at once, followed by a dropwise addition of 36.3 g (239 mmole) of 1,8-diazabicyclo-[5.4.0]undec-7-ene over 5 minutes. The amber colored reaction mixture turned nearly black on addition of the 1,8-diazabicyclo[5.4.0]undec-7-ene. The solution was warmed to 23° C. and stirred 2 hours. The reaction mixture was poured into a separatory funnel containing 300 mL of water. The pH of the aqueous layer was adjusted to 6–7 with hydrochloric acid. The separatory funnel was shaken, and the pH readjusted to 6–7. This process was repeated until a constant pH of 6–7 was maintained in the aqueous layer (30 mL of 12N hydrochloric acid was used). The aqueous and organic layers were separated and the aqueous extract was washed with 300 mL of methylene chloride. The combined organic extracts were washed with 100 mL of saturated, aqueous sodium chloride, dried over 25 g of magnesium sulfate, filtered and concentrated to a dark colored oil. The oil was triturated with 120 mL of 3:1 hexane:diethyl ether. The solvent was decanted providing 21 g of crude (1'S)-2-amino-1,9-dihydro-9-[4-cyano-3-cyclopenten-1-yl]-6-chloropurine dimethylaminal of formula (VIII) as a semi-solid. The semi-solid was dissolved in 150 mL of methylene chloride and vacuum filtered through a 1.5 inch bed of silica gel (50 g). The silica bed was washed four times with 150 mL of 99.5:0.5 methylene chloride:methanol. The filtrates were combined, and concentrated to an oil. Trituration of the oil with 125 mL of diethyl ether provided a solid. The ether was decanted and the solid was dried under vacuum (0.5 mm, 23° C.) for 18 hours to yield 7.6 g (60.8%) of (1'S)-2-amino-1,9-dihydro-9-[4-cyano-3-cyclopenten-1-yl]-6-chloropurine dimethylaminal of formula (VIII). Then 300 mg of this material was dissolved in 25 mL of methanol. The solution was decolorized with 0.5 g of activated carbon (Darco G-60), vacuum filtered through paper and the filtrate was concentrated to give 180 mg of (1'S)-2-amino-1,9-dihydro-9-[4-cyano-3-cyclopenten-1-yl]-6-chloropurine dimethylaminal of formula (VIII) as a colorless foam. The foam was dissolved in 15 mL of hot ethyl acetate. To induce crystallization, the solvent volume was reduced to 10 mL, and to complete crystallization, 5 mL of hexane was added. The crystals were collected by vacuum filtration and dried under vacuum (0.5 mm, 23° C.) for 15 hours to yield 105 mg of the title compound.

mp 177°–180° C.

$[\alpha]_D$+74° (c 0.21, MeOH).

Analysis Found: C(53.21), H(4.51), N(30.99), Cl (11.31); $C_{14}H_{14}ClN_7$ requires: C(53.25), H(4.47), N(31.05), Cl (11.23).

EXAMPLE 4

(1'S)-2-Amino-1,9-dihydro-9-[4-cyano-3-cyclopenten-1-yl]-6H-purin-6-one (Formula (IX), $R^2$=—CN)

A 250 mL round bottomed flask equipped with a reflux condenser and magnetic stir bar was charged with 7.15 g (22.6 mmole) of (1'S)-2-amino-1,9-dihydro-9-[4-cyano-3-cyclopenten-1-yl]-6-chloropurine dimethylaminal, prepared as in Example 3, and 100 mL of 3N hydrochloric acid. The reaction vessel was placed in an oil bath preheated to 75° C. and stirred for 2.5 hours. The dark colored solution was decolorized with 4 g of activated carbon (Darco G-60), then filtered through paper. The charcoal was washed with 50 mL of 3N aqueous hydrogen chloride. The filtrates were combined, and heated to 75° C. To effect crystallization, the pH of the solution was adjusted to 7 with 33 mL of 30% aqueous ammonium hydroxide. To complete crystallization, the reaction slurry was cooled to 23° C. over 30 minutes, then to 0° C. and stirred for 2 hours. The solids were collected by vacuum filtration, washed with 40 mL of 0° C. cooled deionized water, then dried under vacuum (0.5 mm, 23° C.) for 15 hours to yield 3.52 g of (1'S)-2-amino-1,9-dihydro-9-[4-cyano-3-cyclopenten-1-yl]-6H-purin-6-one of formula (IX) where $R^1$=—CN in 64% yield. Then 130 mg was triturated with 5 mL of 100° C., deionized water for 30 minutes, then cooled to 23° C. The solids were collected by vacuum filtration and dried under vacuum (0.5 mm, 23° C.) for 24 hours to yield 110 mg of the title compound.

mp>280° C.

$[\alpha]_D$+41° (c 0.126, DMF).

Analysis Found: C (53.38), H(4.21), N (34.02); $C_{11}H_{10}N_6O \cdot 0.25H_2O$ requires: C(53.54), H(4.29), N(34.06).

EXAMPLE 5

(1'S)-2-Amino-1,9-dihydro-9-[4-carboxyl-3-cyclopenten-1-yl]6H-purin-6-one (Formula (IX), $R^2$=—COOH)

A 250 mL round bottomed flask equipped with a reflux condenser and magnetic stir bar was charged with (3.24 g (13.3 mmole) of (1'S)-2-amino-1,9-dihydro-9-[4-cyano-3-cyclopenten-1-yl]-6H-purin-6-one, prepared as in Example 4, 7.27 g (182 mmole) of sodium hydroxide and 40 mL of deionized water. The reaction flask was placed in an oil bath preheated to 75° C. and stirred for 75 minutes. The hot solution was vacuum filtered through paper and the filtrate was returned to a 250 mL round bottomed flask equipped with a magnetic stir bar. To induce crystallization, the pH of the aqueous solution was carefully adjusted to 3.5 by adding 17 mL of 36% hydrochloric acid. The reaction slurry was stirred for 30 minutes as it cooled to 23° C. To complete crystallization, the slurry was cooled to 0° C. and stirred for 2 hours. The crystals were collected by vacuum filtration, washed with 10 mL of 0° C. deionized water, then 10 mL of ethanol. The crystals were dried under vacuum (0.5 mm, 23 C) for 18 hours to afford 2.77 g (79%) of the title compound, mp>280° C.

$[\alpha]_D + 11° \pm 1$ (c 0.19, DMF).

Analysis Found: C(48.99), H(4.28), N (25.90);

$C_{11}H_{11}N_5O_3 \cdot 0.5H_2O$ requires: C(48.89), H(4.47), N(25.91).

EXAMPLE 6

Synthesis of
(1'S)-2-Amino-1,9-dihydro-9-[4-carbomethoxy-3-cyclopenten-1-yl]-6H-purin-6-one (Formula (IX), $R^2$=—COOCH$_3$)

A 250 mL round bottomed flask equipped with a relux condenser vented to nitrogen atmosphere and magnetic stir bar was charged with 2.70 g (10.3 mmole) of (1'S)-2-amino-1,9-dihydro-9-[4-carboxyl-3-cyclopenten-1-yl]6H-purin-6-one, prepared as in Example 5, 60 mL of methanol and 1.22 g (12.4 mmole) of concentrated sulfuric acid. The reaction solution was placed in an oil bath preheated to 75° C. and stirred for 5.5 hours. The hot reaction mixture was vacuum filtered though paper and the filtrate was transfered to a clean, 250 mL round bottomed flask. The reaction vessel was placed in an oil bath preheated to 65° C. and 1.46 g (14.5 mmole) of triethylamine was added to liberate (1'S)-2-amino-1,9-dihydro-9-[4-carbomethoxy-3-cyclopenten-1-yl ]-6H-purin-6-one from its sulfate salt. To induce crystallization, the reaction mixture was cooled to 23° C. and stirred for 15 hours. The crystals were collected by vacuum filtration, washed with 10 mL of methanol and dried under vacuum (0.5 mm, 23° C.) for 3 hours to yield 2.5 g (88%) of the title compound.

mp 280°–281° C.

$[\alpha]_D + 11°$ (c 0.15, DMF).

Analysis Found: C (52.36), H(4.81), N (25.34);

$C_{12}H_{13}N_5O_3$ requires: C(52.36), H(4.76), N(25.44).

EXAMPLE 7

(1'S)-2-Amino-1,9-dihydro-9-[4-(carbo-1-propyloxy)-3-cyclopenten-1-yl]-6H-purin-6-one (Formula (IX), $R^2$=—COO(CH$_2$)$_2$CH$_3$)

A 500 mL round bottomed flask equipped with a magnetic stir bar and reflux condenser vented to a nitrogen atmosphere was charged with 10.0 g (41.3 mmole) of (1'S)-2-amino-1,9-dihydro-9-[4-cyano-3-cyclopenten-1-yl]-6H-purin-6-one, prepared as in Example 4, 150 mL of 1-propanol and 11 mL (206 mmole) of sulfuric acid. The slurry was heated to 100° C. and stirred at that temperature for 48 hours. The slurry became homogeneous at 90°–100° C. The reaction flask was removed from the heat source and 31.6 mL (227 mL) of triethylamine was added. To induce crystallization, 200 mL of deionized water was added over 5 minutes. The slurry was cooled to 23° C. and stirred for 60 minutes, then to 0° C. and stirred for 4 hours. The solid was collected by vacuum filtration, washed with 10 mL of deionized water and dried under vacuum (0.5 mm, 23° C.) for 18 hours to afford 12.5 g (63%) of the title compound.

mp 256°–258° C.

$[\alpha]_D + 16 \pm 1°$ (c 0.033, methanol).

Analysis Found: C (52.18), H(6.00), N (21.73);

$C_{14}H_{17}N_5O_3 \cdot H_2O$ requires: C(52.33), H(5.96), N(21.79).

EXAMPLE 8

(1'S)-2-amino-1,9-dihydro-9-[4-(hydroxymethyl)-3-cyclopenten-1-yl]-6H-purin-6-one
(Formula (X))

A 3-necked, 2 L round bottomed flask equipped with a reflux condenser vented to a nitrogen atmosphere, addition funnel, thermometer and mechanical stirred was charged with 22.7 g (82.5 mmole) of (1'S)-2-amino-1,9-dihydro-9-[4-carbomethoxy-3-cyclopenten-1-yl]-6H-purin-6-one, prepared as in Example 6, and 100 mL of methylene chloride. The slurry was cooled to 5° C. and 288 mL (288 mmole) of 1M diisobutylaluminum hydride in methylene chloride was added dropwise over 5 minutes. The reaction mixture was stirred at 0° C. for 10 minutes, then warmed to 23° C. and stirred for 20 minutes. Excess diisobutylaluminum hydride was quenched by the gradual addition of 20 mL of 85:15 methanol:acetic acid. The reflux condenser was replaced with a short path distillation head and the reaction mixture was slowly heated to reflux to distill out the methylene chloride. To avoid gelling, a reaction volume of 1000 mL was maintained by a gradual addition of 1050 mL of 85:15 methanol:acetic acid as the methylene chloride was removed by distillation (38° C.). When the distillate temperature rose to 65° C., the distillation head was removed and the reaction vessel was refitted with a reflux condenser vented through a nitrogen atmosphere. The heterogeneous reaction mixture was heated to 65° C., 40 g of diatomaceous earth (Fisher 545) was added and the slurry was stirred for 36 hours. The hot slurry was vacuum filtered through an 8 inch filter funnel and the semi-gelatineous solids were washed three times with 500 mL of methanol. The combined filtrates were concentrated to a volume of 550 mL, then transfered to a 4 neck, 2 L round bottomed flask equipped with a thermometer, mechanical stirrer and addition funnel. To induce crystallization, the reaction mixture was heated to 50° C. and 1 L of methyl t-butyl ether was added dropwise over 30 minutes. The slurry was cooled to 23° C. and stirred for 2 hours. The crystals were collected by vacuum filtration, washed with 50 mL of methyl t-butyl ether and dried under vacuum (0.5 mm, 23° C.) for 15 hours to yield 13.06 g of (1'S)-2-amino-1,9-dihydro-9-[4-(hydroxymethyl)-3-cyclopenten-1-yl]-6H-purin-6-one of formula (X). To obtain a second crop of (1'S)-2-amino-1,9-dihydro-9-[4-(hydroxymethyl)-3-cyclopenten-1-yl]-6H-purin-6-one of formula (X) the filtrate volume was reduced to 350 mL and 500 mL of methyl t-butyl ether was added. The slurry was stirred at 23° C. for 12 hours, the solids were collected by vacuum filtration, washed with 25 mL of methyl t-butyl ether and dried under vacuum (0.5 mm, 23° C.) for 18 hours to yield 3.82 g of a second crop of (1'S)-2-amino-1,9-dihydro-9-[4-(hydroxymethyl)-3-cyclopenten-1-yl]-6H-purin-6-one of formula (X). The first and second crops were blended to afford 16.88 g (83%) of the title compound.

mp>280° C.

$[\alpha]_D + 14°$ (c 0.18, DMF).

Analysis Found: C (51.74), H(5.42), N (27.37);

$C_{11}H_{13}N_5O_2$ requires: C(51.56), H(5.51), N(27.33).

EXAMPLE 9

(1'S)-2-amino-1,9-dihydro-9-[4-(hydroxymethyl)-
3-cyclopenten-1-yl]-6H-purin-6-one
(Formula (X))

A 4-necked, 1 L round bottomed flask equipped with a reflux condenser vented to a nitrogen atmosphere, addition funnel, thermometer and mechanical stirred was charged with 7.70 g (25.4 mmole) of (1'S)-2-amino-1,9-dihydro-9-[4-(carbo-1-propyloxy)-3-cyclopenten-1-yl]-6H-purin-6-one, prepared as in Example 7, and 300 mL of methylene chloride. The slurry was cooled to 5° C. and 88.8 mL (88.8 mmole) of 1M diisobutylaluminum hydride in methylene chloride was added dropwise over 5 minutes. The solution was warmed to 23° C. and stirred for 30 minutes. An additional 6.35 mL (6.35 mmole) of diisobutylaluminum hydride was added to the reaction mixture, and the solution was stirred for 10 minutes. Excess diisobutylaluminum hydride was quenched by the gradual addition of 30 mL of 90:10 methanol:acetic acid. The reflux condenser was replaced with a short path distillation head and the reaction mixture was slowly heated to reflux to distill out the methylene chloride. To avoid gelling, a reaction volume of 400 mL was maintained by a gradual addition of 400 mL of 90:10 methanol:acetic acid as the methylene chloride was removed by distillation (38° C.). When the distillate temperature rose to 65° C., the distillation head was removed and the reaction vessel was refitted with a reflux condenser vented through a nitrogen atmosphere. The heterogeneous reaction mixture was heated to 65° C., 15 g of diatomaceous earth (Fisher 545) was added and the slurry was stirred for 38 hours. The hot slurry was vacuum filtered through a ¾ inch bed of diatomaceous earth (Fisher 545) on an 8 inch filter funnel and the semi-gelatineous solids were washed three times with 300 mL of 90:10 methanol:acetic acid. The combined filtrates were concentrated to a volume of 100 mL, then transferred to a 4 neck, 1 L round bottomed flask equipped with a thermometer, mechanical stirrer and addition funnel. To induce crystallization, the reaction mixture was heated to 50° C. and 350 mL of methyl t-butyl ether was added dropwise over 30 minutes. The slurry was cooled to 23° C. over 30 minutes, then to 0° C. and stirred for 2 hours. The crystals were collected by vacuum filtration, washed with 50 mL of acetonitrile and dried under vacuum (0.5 mm, 23° C.) for 8 hours to yield 4.8 g of (1'S)-2-amino-1,9-dihydro-9-[4-(hydroxymethyl)-3-cyclopenten-1-yl]-6H-purin-6-one of formula (X). To obtain a second crop of (1'S)-2-amino-1,9-dihydro-9-[4-(hydroxymethyl)-3-cyclopenten-1-yl]-6H-purin-6-one of formula (X) the filtrate volume was reduced to 30 mL and 70 mL of methyl t-butyl ether was added. The slurry was stirred at 23° C. for 2 hours, the solids were collected by vacuum filtration, washed with 5 mL of acetonitrile and dried under vacuum (0.5 mm, 23° C.) for 18 hours to yield 1.06 g of a second crop of (1'S)-2-amino-1,9-dihydro-9-[4-(hydroxymethyl)-3-cyclopenten-1-yl]-6H-purin-6-one of formula (X). The first and second crops of (1'S)-2-amino-1,9-dihydro-9-[4-(hydroxymethyl)-3-cyclopenten-1-yl]-6H-purin-6-one of formula (X) were combined and triturated with 50 mL of acetonitrile at 23° C. for 2 hours. The solid was collected by vacuum filtration and dried under vacuum (0.5 mm, 23° C.) for 18 hours to yield 4.43 g (70%) of the title compound.

mp>230° C. (darkens), mp>280° C.

$[\alpha]_D$+13° (c 0.13, DMF).

EXAMPLE 10

(1'S,3'S,4'S)-2-Amino-1,9-dihydro-9-[3,4-dihydroxy-
3-(hydroxymethyl)-1-cyclopentanyl]-6H-6-one
(Formula (I))

A 250 mL round bottomed flask equiped with a magnetic stir bar and reflux condenser vented through a nitrogen atmosphere was charged with 3.35 g (13.5 mmole) of (1'S)-2-amino-1,9-dihydro-9-[4-(hydroxymethyl)-3-cyclopenten-1-yl]-6H-purin-6-one, prepared as in Example 8 or 9, 100 mL of deionized water, 20 mL of acetone and 3.97 g (33.9 mmole) of N-methylmorpholine-N-oxide. The solution was placed in an oil bath preheated to 70° C. and 2.15 mL (0.339 mmole) of a 4 wt % solution of osmium tetraoxide in water was added via syringe. The reaction mixture was stirred at 70° C. for 30 minutes. To decompose the osmium (VI) esters and reduce the higher oxidation osmium (VI, VIII) species, 25 mL of pyridine was added to the reaction mixture followed by hydrogen sulfide gas (purged into the reaction mixture through a fine fritted glass bubbler for 15 seconds). The reaction mixture was stirred at 70° C. and hydrogen sulfide gas was purged into the reaction mixture for 15 seconds after 5, 17, 28, and 52 hours. After stirring a total of 72 hours, 1 g of activated carbon (Darco G-60) was added to the reaction mixture and the hot solution was vacuum filtered through paper. The carbon was washed with 50 mL of deionized water. The filtrate was transferred to a 1 L round bottomed flask and concentrated to a damp, dark solid. The crude solid was triturated with 40 mL of acetonitrile to remove pyridine and N-methylmorpholine, then collected by vacuum filtration to yield 4.8 g of (1'S,3'S,4'S)-2-amino-1,9-dihydro-9-[3,4-dihydroxy-3-(hydroxymethyl)-1-cyclopentanyl]-6H-6-one as a dark colored solid. The dark solid was transferred to a 250 mL round bottomed flask equipped with a magnetic stir bar and reflux condenser, then dissolved in 160 mL of 4:1 deionized water:ethanol. The dark colored solution was heated to 70° C. then treated with 1.5 g of activated carbon (Darco G-60). The hot slurry was vacuum filtered through a ½ inch bed of diatomaceous earth (10 g) in a steam jacketed filter funnel. The solids were washed with 25 mL of deionized water. To induce crystallization, the filtrate volume was reduced to 70 mL. To complete crystallization, the slurry was stirred for 1 hour at 23° C., then cooled to 0° C. and stirred 1 hour. The crystals were collected by vacuum filtration, washed with 10 mL of ethanol and dried under vacuum (0.5 mm, 23° C.) for 15 hours to yield 2.9 g of (1'S,3'S,4'S)-2-amino-1,9-dihydro-9-[3,4-dihydroxy-3-(hydroxymethyl)-1-cyclopentanyl]-6H-6-one of formula (I). To further reduce the osmium content, the 2.9 g of (1'S,3'S,4'S)-2-amino-1,9-dihydro-9-[3,4-dihydroxy-3-(hydroxym ethyl)-1-cyclopentanyl]-6H-6-one of formula (I) was transferred to a 250 mL round bottomed flask equiped with a magnetic stir bar and reflux condenser, then dissolved in 50 mL of deionized water containing 2.65 mL of 36% hydrochloric acid. The reaction flask was placed in an oil bath preheated to 70° C. and the solution was purged with hydrogen sulfide gas for 30 seconds. The solution was stirred at 70° C. for 20 hours, then vacuum filtered through paper. The filtrate was transfered to a 250 mL round bottomed flask, heated to 70° C. and the pH of the solution was adjusted to 7 by adding 6 mL of 30% aqueous ammonium hydroxide. Activated carbon (Darco G-60, 1 g) was added to the reaction mixture and the hot solution was vacuum filtered through a ½ inch bed of diatomaceous earth (10 g) in a steam jacketed filter funnel. The solids were washed two times with 20 mL of deionized water. The filtrates were combined in a 250 mL round bottomed flask. To induce crystallization, the solvent volume was reduced to 40 mL, the resulting slurry was stirred for 1 hour at 23° C., then cooled to 0° C. and stirred for 1 hour. The crystals were collected by vacuum filtration, washed with two times 10 mL of deionized water, 10 mL of ethanol then dried under vacuum (0.5 mm, 23° C.) for 18 hours to yield 2.33 g (61%) of the title compound.

mp>215° C., shrank into decomposition $[\alpha]_D +14°$ (c 0.133, $H_2O$)

Analysis Found: C (44.19), H(5.69), N (23.43); $C_{11}H_{15}N_5O_4 \cdot H_2O$ requires: C(44.15), H(5.73), N(23.40).

What is claimed is:

1. A compound 1,8-diazabicyclo[5.4.0]undec-1(7)-enium cyanide.

2. The method of generating the compound of claim 1, wherein acetone cyanohydrin and 1,8-diazabicyclo[5.4.0]undec-7-ene are combined in methylene chloride at about 0° C.

* * * * *